United States Patent
Gellman

(10) Patent No.: US 8,591,538 B2
(45) Date of Patent: *Nov. 26, 2013

(54) SELF-EXPANDING CANNULA AND A METHOD FOR APPLYING AND POSITIONING A SELF-EXPANDING CANNULA

(75) Inventor: Barry N. Gellman, North Easton, MA (US)

(73) Assignee: Thoratec LLC, Pleasanton, CA (US)

( * ) Notice: Subject to any disclaimer, the term of this patent is extended or adjusted under 35 U.S.C. 154(b) by 617 days.

This patent is subject to a terminal disclaimer.

(21) Appl. No.: 11/701,149

(22) Filed: Jan. 31, 2007

(65) Prior Publication Data

US 2007/0233041 A1 Oct. 4, 2007

Related U.S. Application Data

(60) Provisional application No. 60/787,740, filed on Mar. 30, 2006.

(51) Int. Cl.
*A61M 29/00* (2006.01)

(52) U.S. Cl.
USPC .......................................................... 606/194

(58) Field of Classification Search
USPC ......... 606/184, 200, 198, 194, 185, 159, 127, 606/108, 1; 623/2.38, 2.37, 2.18, 2.11, 623/1.46, 1.42, 1.35, 1.24, 1.22, 1.2, 1.16, 623/1.15, 1.12, 1.11, 1.53, 1.13, 1.18, 1.19, 623/1.23, 1.52; 604/96.01, 93.01, 9, 7, 604/6.16, 6.11, 6.01, 532, 523, 509, 508, 604/506, 43, 264, 167.06, 164.03, 164.01, 604/103.09, 101.05, 104–109; 600/36, 18, 600/121, 184; 29/447, 446

See application file for complete search history.

(56) References Cited

U.S. PATENT DOCUMENTS

| 4,318,401 A | 3/1982 | Zimmerman |
| 4,417,888 A | 11/1983 | Cosentino |

(Continued)

FOREIGN PATENT DOCUMENTS

| EP | 0078565 A1 | 5/1983 |
| EP | 1523948 A1 | 4/2005 |

(Continued)

OTHER PUBLICATIONS

Mueller, Xavier M., et al., "Optimized Venous Return of Self-Expanding Cannula: From Computational Fluid Dynamics to Clinical Application;" 2002; *Interactive Cardiovascular and Thoracic Surgery*; vol. 1; pp. 23-27.

(Continued)

*Primary Examiner* — Ryan Severson
*Assistant Examiner* — Tin Nguyen
(74) *Attorney, Agent, or Firm* — Kilpatrick Townsend & Stockton LLP

(57) ABSTRACT

A self-expanding cannula providing a conduit through a skin between an inside of a corpus and an outside of the corpus is disclosed. The self-expanding cannula includes a body encompassing a lumen, and has a distal-end to be positioned outside of the corpus for attachment to an extracorporeal fluid handling system and having a proximal-end to be positioned inside of the corpus, for attachment to an organ of an human or an animal. The body of the self-expanding cannula is constructed from a braided-wire, so that the self-expanding cannula is capable of expanding from a closed diameter to an opened diameter. A catheter-sheath and a catheter-sheath-assembly as well as to a method for applying and positioning a self-expanding cannula, and a catheter-sheath-assembly are disclosed.

21 Claims, 7 Drawing Sheets

(56) References Cited

U.S. PATENT DOCUMENTS

| | | | |
|---|---|---|---|
| 5,037,427 A | 8/1991 | Harada | |
| 5,312,417 A | 5/1994 | Wilk | |
| 5,431,676 A | 7/1995 | Dubrul | |
| 6,083,257 A | 7/2000 | Taylor | |
| 6,136,025 A | 10/2000 | Barbut | |
| 6,156,064 A * | 12/2000 | Chouinard | 623/1.44 |
| 6,485,513 B1 * | 11/2002 | Fan | 623/1.36 |
| 6,712,842 B1 * | 3/2004 | Gifford et al. | 623/1.13 |
| 6,866,805 B2 | 3/2005 | Hong | |
| 2002/0002360 A1 | 1/2002 | Orth | |
| 2002/0188201 A1 * | 12/2002 | Crowley | 600/439 |
| 2003/0074049 A1 * | 4/2003 | Hoganson et al. | 623/1.13 |
| 2003/0092984 A1 | 5/2003 | Weber | |
| 2004/0059277 A1 * | 3/2004 | Maguire et al. | 604/6.16 |
| 2004/0103516 A1 * | 6/2004 | Bolduc et al. | 29/446 |
| 2004/0193241 A1 * | 9/2004 | Stinson | 623/1.2 |
| 2004/0199121 A1 | 10/2004 | Wenchell | |
| 2005/0033417 A1 * | 2/2005 | Borges et al. | 623/1.46 |

FOREIGN PATENT DOCUMENTS

| | | |
|---|---|---|
| WO | WO 01/37921 A1 | 5/2001 |
| WO | 2004/096095 A2 | 11/2004 |
| WO | WO 2004096095 A2 * | 11/2004 |
| WO | WO 2005/002454 A1 | 1/2005 |

OTHER PUBLICATIONS

Office Action from U.S. Appl. No. 11/701,277 dated Feb. 5, 2009.

* cited by examiner

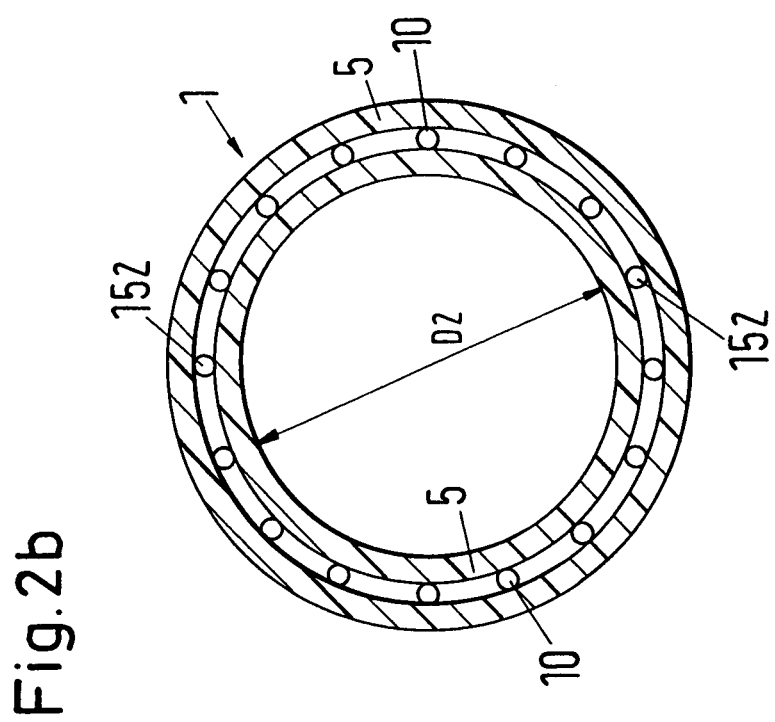

SELF-EXPANDING CANNULA AND A METHOD FOR APPLYING AND POSITIONING A SELF-EXPANDING CANNULA

CROSS-REFERENCES TO RELATED APPLICATIONS

This application claims the priority of Provisional patent application No. 60/787,740, filed Mar. 30, 2006, the disclosure of which is incorporated herein by reference.

BACKGROUND OF THE INVENTION

The invention relates to self-expanding cannula, a catheter-sheath, a catheter-sheath-assembly and a method for applying a self-expanding cannula, a catheter-sheath and a catheter-sheath-assembly.

This disclosure provides a means to enable percutaneous access for a cannula, in particular for a cardiac cannula positioned in the heart and/or a major vessel and/or other organs utilized for extracorporeal communication of a fluid. This device provides a conduit communicated between the fluid supply extending outside of the body and provides passage of fluids in and out of the body. The self-expandable cannula in its collapsed or compressed state has a small diameter for introduction and positioning and expands to a relatively large bore conduit for fluid flow.

Medical devices such as cardiac cannulae or other medical devices are typically placed under direct vision into major blood vessels and/or the heart of a patient for the purpose of providing a fluid conduit to and from an extracorporeal circuit.

The most common techniques used in Cardiac Surgery Centers for postcardiotomy support include Extracorporeal Membrane Oxygenation (ECMO) and Ventricular Assist Devices (VAD). Poor ventricular function may be diagnosed preoperatively or may have resulted from myocardial insult during surgery (i.e. inadequate perfusion, crossclamping for extended periods of time limiting reperfusion, injury, etc.). Reduced cardiac output will affect other organs due to low blood pressure and blood flow.

Over time, allowing the myocardium to rest may allow recovery. Otherwise, the patient may require long-term cardiac support. Patients who cannot be weaned from cardiopulmonary bypass and possess isolated ventricular dysfunction are probably candidates for a Ventricular Assist Device (VAD). BiVAD support will require two-pump circuits. When pulmonary dysfunction occurs, the patient is most likely a candidate for ECMO.

Cardiac cannulae provide the patient interface means to an extracorporeal blood circuit. Placement of these cannulae may access the vasculature through major vessels (Right Atrium (RA), Left Atrium (LA), Left Ventricular Apex (LVA), Femoral Artery (FA), Femoral Vein (FV), Superior Vena Cava (SVC), Inferior Vena Cava (IVC) or the Aorta). Two cannulae are required in the extracorporeal circuit—one for blood outflow and one for blood return.

In open chest procedures, the blood inlet (to the pump) cannula is passed through a dilated tunnel created from the ventricle through the subcutaneous plane to the percutaneous access site. The blood return cannula (from the pump) is passed through a dilated tunnel created from the arch of the ascending aorta through the subcutaneous plane to the percutaneous exit site. The percutaneous access sites are located ipsilaterally, on the left abdominal wall for the LVAD, in the medial anterior position. The location is ipsilateral on the right abdominal wall for an RVAD, in the medial anterior position.

The extracorporeal system is attached to the cannulae using good perfusion technique. Cannulae placed within the thorax are typically secured in place to prevent accidental dislodgement which could result in a catastrophic condition. Purse-string sutures and stabilizer grommets often provide security until tissue healing occurs. As such, cannulae removal and/or exchange requires a second surgery under direct visualization. The open chest wound is closed upon successfully administrating the support system.

A problem, which is up to now not yet solved in a satisfactory way, is that the cannulae, which must be introduced into and tunneled through the tissue of the corpus of a patient to get access to the heart, an associate vessel or to an other organ, very often have a comparatively large diameter. Among further things, such a large cannula diameter can affect the skin, tissue or the respective organs to be accessed very negatively and can cause lasting injuries. What is more, it is understood, is that a large cannula diameter complicates and makes the tunneling of the cannula difficult.

SUMMARY OF THE INVENTION

It is therefore an object of the present invention to provide a cannula and a method for tunneling and positioning a cannula, in particular a cardiac cannula, in a corpus of a patient, enabling a very easy access to an organ in a very conservative manner.

The subject matter of the invention which satisfies these objects is characterized by the features disclosed herein.

Respective subordinate features also disclose particularly advantageous embodiments of the invention.

An embodiment of the invention thus relates to a self-expanding cannula, in particular a self-expanding cardiac cannula, providing a conduit through a skin between an inside of a corpus and an outside of the corpus. The self-expanding cannula includes a body encompassing a lumen extending essentially axially along a center-line, and has a distal-end to be positioned outside of the corpus for attachment to an extracorporeal fluid handling system, in particular to a blood handling system comprising a blood pump, and having a proximal-end to be positioned inside of the corpus, for attachment to an organ of a human or an animal, in particular for attachment to a wall of a heart or to the wall of an associated vessel. The body of the self-expanding cannula is constructed from a braided-wire, so that the self-expanding cannula is capable of expanding from a closed diameter to an opened diameter.

The self-expanding cannula in accordance with the present invention is essentially a wire braided tube covered with a flexible membrane such to effect a leak-tight conduit capable of self-expanding from a closed diameter to an opened diameter.

The self-expanding cannula is preferably positioned under direct visualization during open chest surgery with the proximal-end of the self-expanding cannula for example positioned in a wall of a heart or major vessel of a human patient or an animal, the body of the self-expanding cannula tunneled in the corpus of the patient or the animal and a distal-end emerging through the skin to externally communicate the lumen. Preferably, the self-expanding cannula is kept compressed in a catheter-sheath while introducing it into the corpus of a patient, and having a small closed diameter requiring minimal tissue puncture due to the small device profile.

That is, using a self-expanding cannula in accordance with the present invention allows to apply and position a cannula within a human or an animal corpus in a very easy and conservative way. Before positioning the self-expanding cannula within the corpus, the self-expanding cannula may have a comparatively considerable diameter in an un-compressed state, and having in a compressed state a comparatively small closed diameter, the self-expanding cannula is preferably placed in a catheter-sheath in the compressed state and is first positioned within the corpus of the patient, only requiring a small tunnel through the skin and the tissue of the corpus due to the small diameter of the self-expanding cannula in the closed state. After having positioned the self-expanding cannula within the corpus, the catheter-sheath is removed and the self-expanding cannula expands to its larger opened diameter.

In a special embodiment of a self-expanding cannula in accordance with the present invention, which is very important in practice, a pre-determinable portion of the braided-wire is covered by a flexible membrane, which is preferably an elastomeric material creating a membrane-like structure enabling the braided-wire to articulate from the closed diameter to the opened diameter and the flexible membrane sealing an interstitial space resultant between the braid openings. The flexible membrane is positioned inside of the braided-wire and/or outside of the braided-wire; that is, the flexible membrane can, in a special embodiment, close about the braided-wire.

A further important advantage of the flexible membrane is that the self-expanding cannula can be tunneled through the skin, the tissue and a wall of the heart, the vessel or a wall of an organ of a patient in a very conservative and easy manner because, due to the flexible membrane, the surface of the self-expanding cannula becomes smooth and very tissue-friendly.

Regarding another embodiment of the present invention, in the applied state a pre-determinable velour-portion of the self-expanding cannula emerging through the skin of the corpus is contained within a velour-like tube to enable a tissue in-growth of the skin, in particular to reduce bacterial wicking about the wound. The velour material is preferably knitted and/or woven polyester and/or the velour-portion is bonded as a velour-tube to an outside diameter of the self-expanding cannula. A knitted material structure will expand and contract more easily than a woven structure and would be preferred at the skin site. The velour-tube is preferably bonded to the outside diameter of the self-expanding cannula.

The lumen of the self-expanding cannula can be larger than the blood vessel it is positioned in, as it will only expand to the maximum allowable diameter. In a special embodiment, the distal-end of the self-expanding cannula may be bell-mouthed to reduce aspiration tip shear or jet discharge.

In a further embodiment, the proximal-end of the self-expanding cannula includes a bare-section which does not contain the flexible membrane in order to provide a flow of a fluid, in particular of blood, into and/or out of the self-expanding cannula, in particular in order to reduce shear on the blood.

Preferably, the individual wire is individually coated in the bare-section. Regarding another embodiment, the proximal-end of the self-expanding cannula also comprises a flexible membrane, wherein a hole is provided in the flexible membrane at the proximal-end of the self-expanding cannula in order to permit a flow of a fluid, in particular of blood, into and/or out of the self-expanding cannula, in particular to reduce shear on the blood.

That is, there are different special embodiments which can be advantageously used in practice. The flexible membrane may extend the entire length of the cannula. Alternatively, the membrane may protrude a partial distance along the cannula length with no membrane towards only the proximal-end. Non-covered segments of the self-expanding cannula will provide flow into or out of the cannula to reduce shear on the blood. In addition, non-covered segments will prevent localized aspiration of the vessel wall into the cannula on the inflow cannula as well as jet streaming on the outflow cannula. Alternatively, holes placed in the membrane between the wires could also perform this same function. If constructed with holes and utilizing a separable membrane between the inner and outer surfaces, the periphery of the hole should preferably be sealed to prevent blood flow between the flexible membrane layers.

A distal wire-end of a self-expanding cannula in accordance with the present invention is closed-ended, in particular closed-ended accomplished by a fold of the wire, and/or includes a welded joint end or a coating, especially a polymer coating joining the wire.

The flexible membrane, and/or the closed-ended accomplished by a fold of the wire and/or including a welded joint end and/or the coating, and/or the polymer coating joining the wire, is fabricated from polyurethane and/or vinyl and/or a thermoplastic rubber and/or a natural rubber and/or a thermoset material, in particular urethane, and/or the flexible membrane is dip molded and/or blown film and/or extruded and/or injection molded and/or pultruded and/or assembled from flat stock as a separate component and/or assembled to the braided body and/or the flexible membrane is applied about the braided-wire by dipping and/or by coating the braided-wire with liquid polymer and/or the flexible membrane is spray applied to the braided-wire. The preferred material for the flexible membrane is urethane. As already mentioned, the flexible membrane may be positioned outside the braided-wire, inside the braided-wire or both inside and outside, or the braided-wire may be embedded within the flexible membrane.

Regarding a special embodiment, the wire is braided to a loose pitch ranging from 0.5" to 4", in particular from 0.6" to 3", especially from 0.75" to 1.5", and/or preferably a target length of the wire is 1" pitch for a diameter in order to allow the self-expanding cannula to dilate to 0.5" diameter and/or wherein in a compressed state a diameter ranges from 0.03" to 0.15", in particular from 0.06" to 0.10", preferably about 0.08".

To avoid misunderstandings, it is noted that the dimension unit 1" is used in the usual way, that is 1"=1 in =1 inch which equals 2.54 cm.

The number of wires utilized in the over-under braid preferably, but not necessarily, ranges from 5 to 100 wires, in particular from 20 to 48 wires, preferably from 24 to 32 wires, and/or about half of the wires are left-hand wind and about half of the wires are right-hand wind and/or a wire-diameter of a strand is between 0.001" to 0.02", in particular 0.003" to 0.01, preferably about 0.005", and/or the wire is made of plastic, and/or made of a composite material, and/or made of a metal, especially made of a stainless steel, preferably made of at least ½ hard stainless steel and/or made of NITINOL and/or titanium and/or tantalum and/or of another suitable material.

It is understood that the pitch, wire diameter, number of wires, braid pattern, compressed diameter, and expanded diameter are not limited to these dimensions and will be a function of tightness of braid resultant dimensions desired, strength of spring rate of the coil and other important parameters.

In a further important embodiment, the self-expanding cannula in accordance with the present invention is pre-assembled at a certain diameter into a catheter-sheath wherein the catheter-sheath may or may not include a depth-marker, in particular a depth-marker-band for positioning a proximal-end of the catheter-sheath in the corpus and/or the catheter-sheath includes a pusher-device for catheter-sheath removal after positioning the self-expanding cannula within the corpus.

Thus, in the compressed state the self-expanding cannula is preferably pre-assembled into the catheter-sheath. Contained within the catheter-sheath can also be a pusher-device for sheath removal once the assembly is positioned within the body and the distal-end externalized. Placement of the self-expanding cannula would be performed with the catheter-sheath in place. It is envisioned that the catheter-sheath would be placed within the body cavity and the distal-end tunneled to emerge out the desired percutaneous site. Once accomplished, the heart (or major vessel) would be entered by poking the device through the wall. Depth placement for positioning of the proximal-end can be identified by marker-bands about the catheter-sheaths.

In another embodiment according to the present invention, at a distal externalized portion of the self-expanding cannula a tissue dilating means is provided to maintain the self-expanding cannula open as it transitions the vessel wall, and/or surrounding muscles and/or fat and/or the skin.

Regarding a very important embodiment, in a pre-settable adjusting-portion of the self-expanding cannula a spring rate of the braided-wire and/or of the flexible membrane and/or a hoop stress of the self-expanding cannula is set to a pre-settable value by adjusting or choosing, respectively, a wire-diameter and/or a number of wires of the braided-wire and/or by adjusting the configuration of the wires in the braided-wire and/or by adjusting the pitch and/or the diameter of the wire and/or by adjusting an elasticity of the flexible membrane so that the self-expanding cannula is tailored to perform a low pressure safety valve, in particular a low pressure safety valve in a blood pump circuit, in order to auto-regulate a flow rate of a fluid, especially a flow rate of blood through the self-expanding cannula.

Preferably, the adjusting-portion is balanced to automatically adjust an effective diameter of the self-expanding cannula under pressures ranging from 10 mmHg to 180 mmHg, preferably under pressures ranging from 20 mmHg to 140 mmHg on the inflow side of an externally attached pump.

That is, the self-expanding cannula, which can be a pump inflow cannula, can be tailored to perform a low pressure safety valve in a blood pump circuit. Should a sudden low flow condition occur that could temporarily starve the pump of fluid, a high negative pressure can result in deleterious effects on the blood. Providing a cannula that would automatically compensate for changes in pressure would reduce blood damage. As such, a reduction in flow to the pump produces an increase in draw pressure which would result in reducing the cannula diameter to auto-regulate the flow rate to match the available blood supply and move the pressure drop away from the heart down the cannula. To accomplish this, the spring rate of wire windings should be built into the braided structure and flexible membrane. The wire diameter, number of wires and configuration, pitch, diameter and elasticity of the membrane will all affect the hoop stress of the tubular conduit. The assembly components must be balanced to automatically adjust the effective cannula diameter (or portion thereof) under pressures ranging from 20 mmHg to 140 mmHg on the inflow side of the pump. The cannula would be fabricated "normally open" and actively constrict under lesser pressures in the lumen.

Another alternative is the use of the wire selected for the conduit. A NITINOL shape memory metal could be utilized to enable the conduit to expand to full utility from body heat (37° C.) when the sheath is removed from the structure. However, this special embodiment of the present invention negates the ability to auto-regulate the fluid flow.

To assist the positioning of the proximal-end of the self-expanding cannula, a pull-wire may be provided, e.g. between an inner and an outer flexible membrane, in order to steer the proximal tip of the self-expanding cannula to better guide it in a pre-settable position.

The invention also relates to a catheter-sheath for pre-assembling a self-expanding cannula as described above in great detail.

In a special embodiment, the catheter-sheath includes a pusher-device for removal of the self-expanding cannula after positioning the self-expanding cannula within a human or an animal corpus and/or includes a depth-marker, in particular a depth-marker-band for positioning a proximal-end of the catheter-sheath in the corpus.

Furthermore, the invention relates to a catheter-sheath-assembly including a catheter-sheath as already described.

The invention relates also to a method for applying and positioning a self-expanding cannula within a human or an animal corpus, and/or a method for positioning a catheter-sheath, and/or a method for positioning a catheter-sheath-assembly in accordance with the present invention, including the following steps:

providing a self-expanding cannula in accordance with the present invention;

positioning a proximal-end of the self-expanding cannula in a wall of a heart and/or a major vessel;

tunneling a distal-end of the self-expanding cannula through a skin of the corpus to externally communicate a lumen of the self-expanding cannula; and/or including the following steps:

providing a self-expanding cannula in accordance with the present invention;

tunneling a distal-end of the self-expanding cannula through a skin of the corpus to externally communicate a lumen of the self-expanding cannula;

positioning a proximal-end of the self-expanding cannula in a wall of a heart and/or a major vessel.

In a special embodiment of a method according to the present invention, the self-expanding cannula is placed through an open chest method, in particular placed into a vasculature through a normal Seldinger technique and/or through a modified Seldinger technique and/or is advanced through the vasculature to a desired position within the heart.

A maneuvering within an atrium and/or a ventricle and/or a pulmonary vein to set a proximal-end-position of the self-expanding cannula can be performed by using a fluoroscopic visualization technique and/or the proximal positioning of the self-expanding cannula is accomplished by using a guide-wire and/or the guidance of a Swan-Ganz catheter previously positioned to a desired location.

In another embodiment of a method according to the present invention, which is very important in practice, the self-expanding cannula is pre-assembled and compressed into a catheter-sheath forming a catheter-sheath-assembly, requiring minimal tissue puncture due to a small profile of the catheter-sheath-assembly. The catheter-sheath-assembly may especially be placed within a corpus-cavity. A distal-end of the catheter-sheath-assembly is tunneled to emerge out the desired percutaneous site of the corpus, a heart and/or an associated vessel, in particular a major vessel is entered by poking the catheter-sheath-assembly and/or the self-expanding cannula through a wall of the heart and/or the associated vessel and/or a proximal-end of the catheter-sheath-assembly and/or of the self-expanding cannula is positioned by using a depth-marker, in particular a depth-marker-band, provided about the catheter-sheath.

Preferably, the catheter-sheath includes a pusher-device and the self-expanding cannula is passively dilated with the catheter-sheath removed from the outside of the self-expanding cannula by the pusher-device, once the self-expanding cannula is positioned within the corpus and/or once the distal-end of the self-expanding cannula is externalized.

The distal-end of the self-expanding cannula may be secured to an extracorporeal circuit, in particular to an extracorporeal circuit including a blood pump, and the proximal-end of the self-expanding cannula may or may not be fixed by a suture at a wall of the heart and/or of an associate vessel and/or at a tissue of the corpus.

In special cases, the self-expanding cannula may be used to access a kidney, a bladder, a G.I. tract, in particular an intestine, a stomach, or an esophagus, a thorax cavity or a sinus.

BRIEF DESCRIPTION OF THE DRAWINGS

In the following, the invention will be explained in more detail with reference to the drawings.

FIG. 2b shows a cross-sectional view of a special embodiment according to FIG. 2a;

DESCRIPTION OF THE PREFERRED EMBODIMENTS

Figure 1:
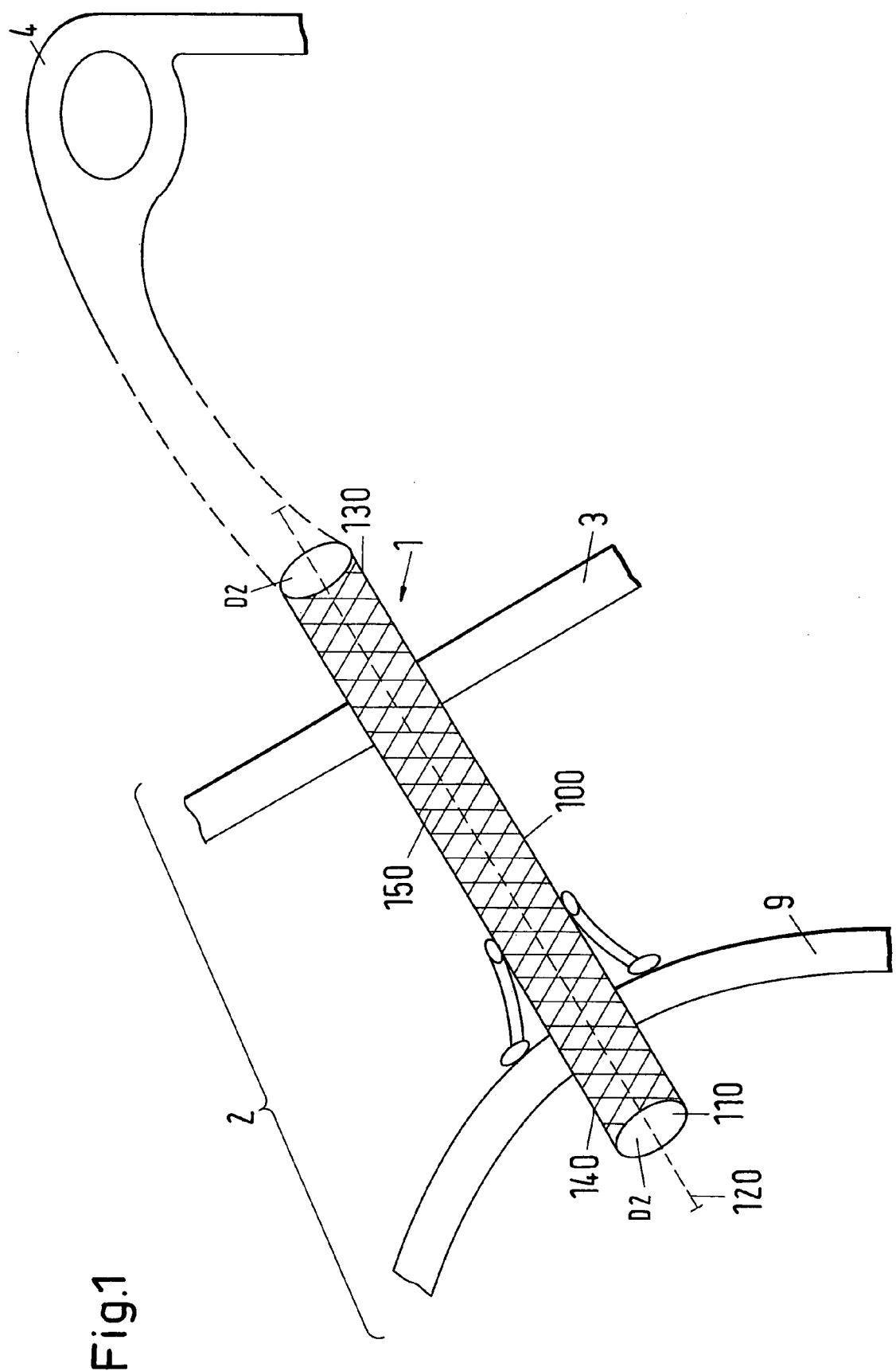
FIG. 1 shows a self-expanding cannula applied within a patient's corpus.

In FIG. 1 a self-expanding cannula according to the present invention being applied within a patient's corpus is schematically displayed, which self-expanding cannula will be designated in the following by the reference number 1.

The self-expanding cannula 1 providing a leak-tight conduit through a skin 3 between an inside of a corpus 2 and an outside of the corpus 2 includes a body 100 encompassing a lumen 110 extending essentially axially along a center-line 120, and having a distal-end 130 which is in FIG. 1 positioned outside of the corpus 2, and attached to an extracorporeal fluid handling system 4, which is in the present example an extracorporeal blood handling system 4 including a blood pump. A proximal-end 140 of the self-expanding cannula 1 is in the example of FIG. 1 positioned inside of the corpus 2 at a wall 9 of a heart of a patient, so that a blood flow can be established through the lumen 110 from the distal-end 130 from the blood pump outside of the corpus 2 via the proximal-end 140 through the inside of the corpus 2 and into the heart of the patient, thus providing a means for a blood exchange between a chamber of the heart and an external device, e.g. to the blood pump of the blood handling system 4.

Figure 2A:
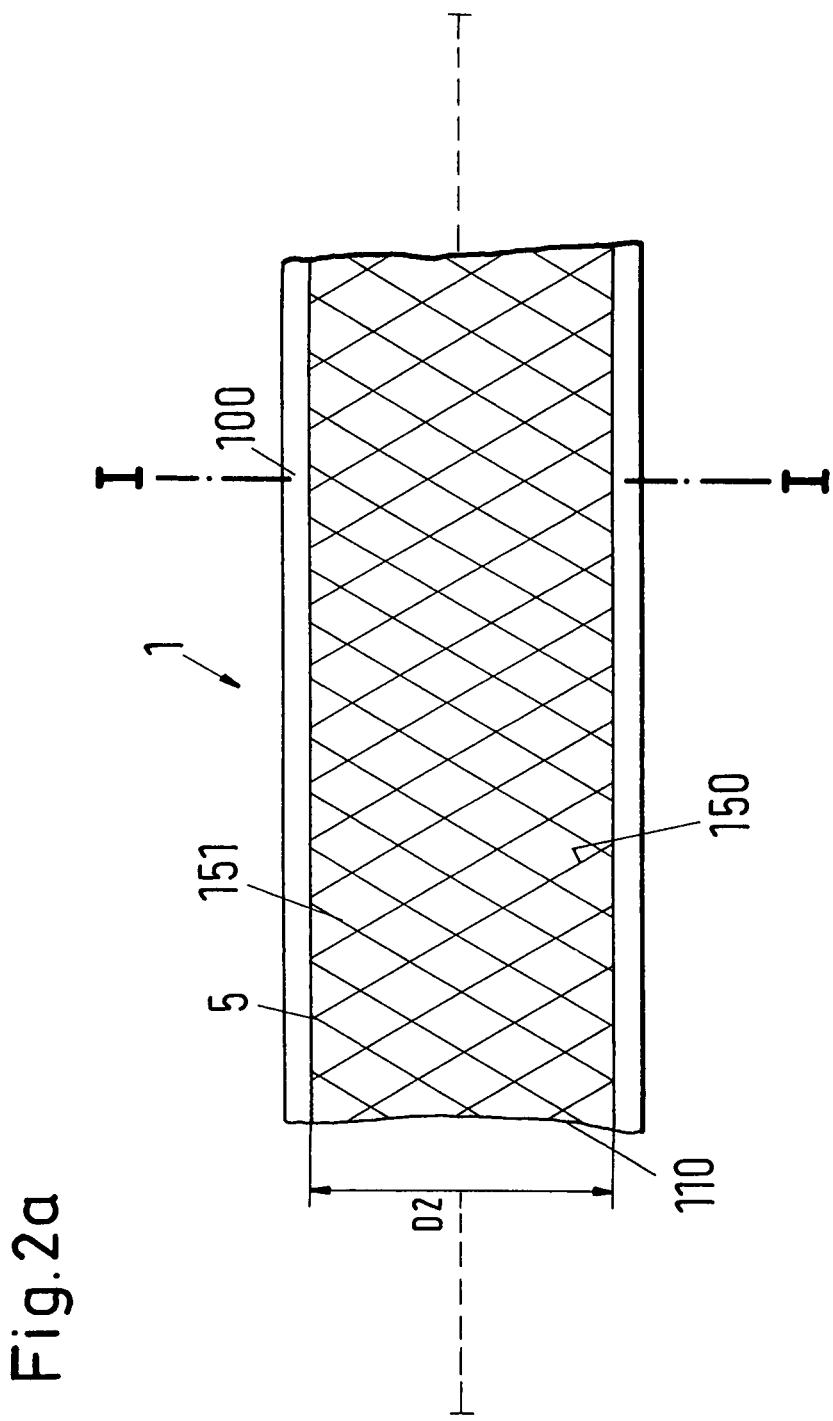
FIG. 2a shows a self-expanding cannula including a flexible membrane.

The embodiment of a self-expanding cannula 1 shown in FIG. 2a includes a flexible membrane 5. Regarding this embodiment, which is very important in practice, a pre-determinable portion of the body 100 and the braided-wire 150, respectively, is covered by the flexible membrane 5 enabling the braided-wire 150 to articulate from the closed diameter D1 to the opened diameter D2 and, additionally, the flexible membrane 5 can seal an interstitial space 151 resultant between the braid openings.

Figure 2C:
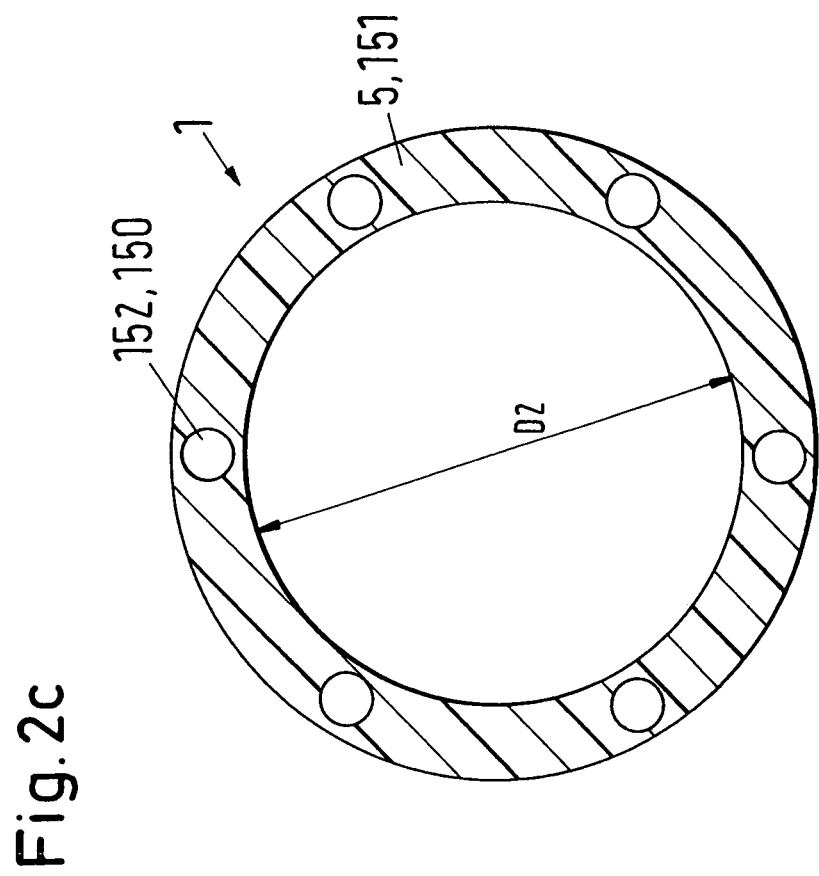
FIG. 2c shows a further embodiment according to FIG. 2b.

A very important advantage of the self-expanding cannula 1 according to FIGS. 2a-2c having a flexible membrane 5, which is preferably made of an elastomeric material creating the membrane-like structure, is that the self-expanding cannula 1 can be tunneled through the skin 3, the tissue and a wall 9 of the heart of the patient, or the vessel, or a wall of an organ in a very conservative and easy manner because due to the properties of the flexible membrane 5 the surface of the self-expanding cannula 1 becomes smooth and very tissue-friendly.

In FIG. 2b a special embodiment of a self-expanding cannula 1 having the flexible membrane 5 is displayed in a cross-sectional view with respect to line I-I according to FIG. 2a. A pre-determined portion of the braided-wire 150 is covered by the flexible membrane 5, wherein the flexible membrane 5 is positioned both inside of the braided-wire 150 and outside of the braided-wire 150. It is understood that in another embodiment the flexible membrane 5 may only be present inside or only be present outside of the braided-wire 150.

The special embodiment of FIG. 2b also includes two pull-wires 10 provided between the inner flexible membrane 5 and the outer flexible membrane 5 enabling the steering of the proximal tip of the self-expanding cannula 1 to better guide it in a pre-settable position.

In FIG. 2c a further embodiment according to FIG. 2b is displayed, wherein the braided-wire 150 is completely encompassed by the flexible-membrane 5; that is, the braided-wire 150 or the individual wires 152 form an inlet within the flexible membrane 5.

Figure 3:
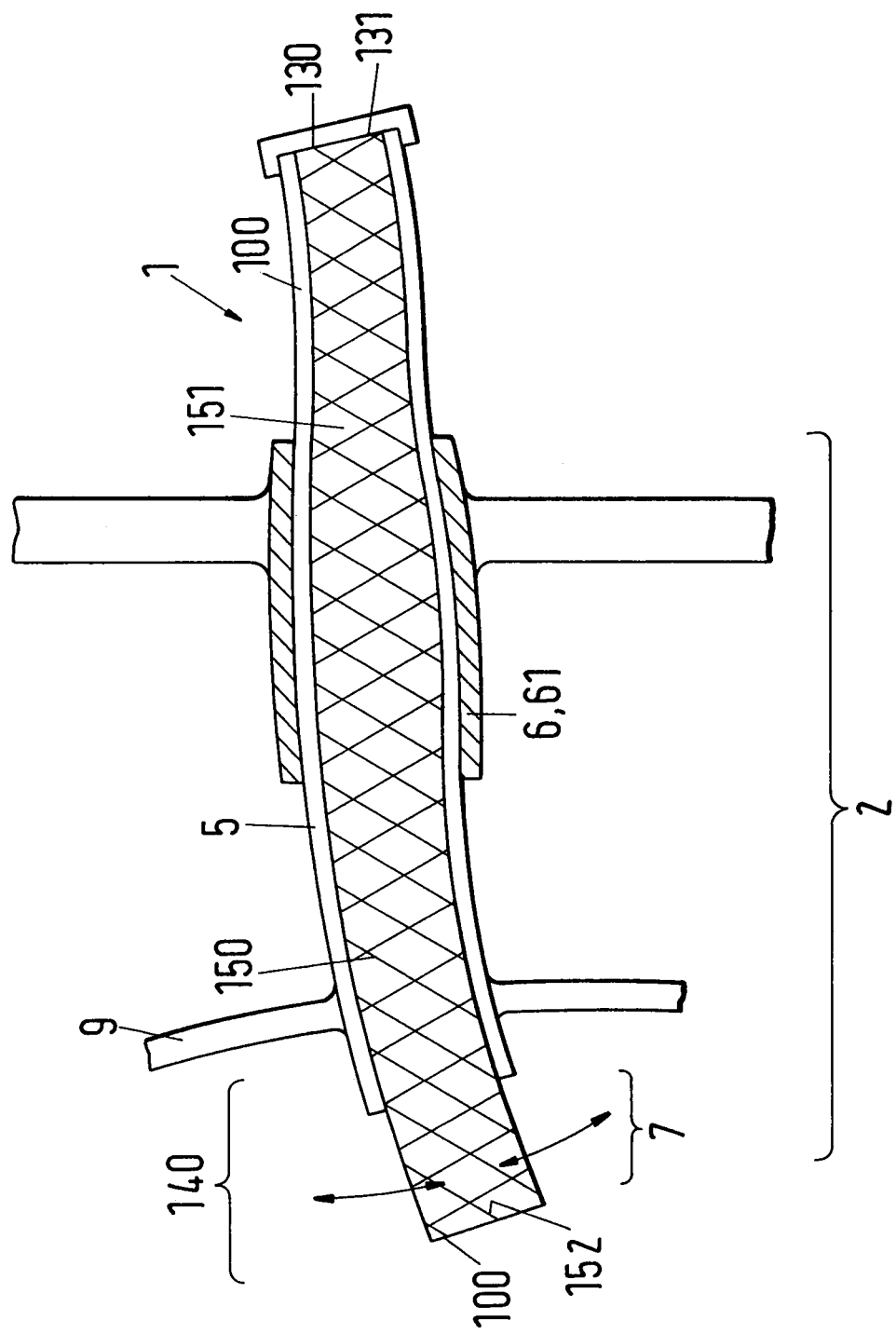
FIG. 3 shows a self-expanding cannula with a velour-portion in the applied state.

In FIG. 3 a self-expanding cannula 1 is displayed in the applied state, comprising a velour-portion 6 in a pre-determinable portion of the body 100 of the self-expanding cannula 1.

In the example of FIG. 3 the pre-determinable velour-portion 6 of the self-expanding cannula 1 is emerged through the skin 3 of the corpus 2, and is contained within a velour-like tube 61 to enable a tissue in-growth of the skin 3, in particular to reduce bacterial wicking about the wound. Preferably, the velour material is knitted and/or woven polyester and the velour-portion 6 is bonded as a velour-tube 61 to an outside diameter of the self-expanding cannula 1.

The proximal-end 140 of the self-expanding cannula 1 includes a bare-section 7 which is placed behind the wall 9 in the heart of a patient. The bare-section 7 does not contain the flexible membrane 5 in order to provide a flow of blood into and/or out of the self-expanding cannula, in particular to reduce shear on the blood.

Preferably, but not necessarily, in the bare-section 7 the individual wire 152 is individually coated, which is not the case in the example of FIG. 3.

The distal wire-end 131 of the self-expanding cannula 1 according to FIG. 3 is closed-ended by a welded joint. It is understood that in another embodiment the closed-end of the distal wire-end 131 can be accomplished by a fold of the wire, and/or may include a welded joint end or a coating, especially a polymer coating joining the wire.

Figure 4A:
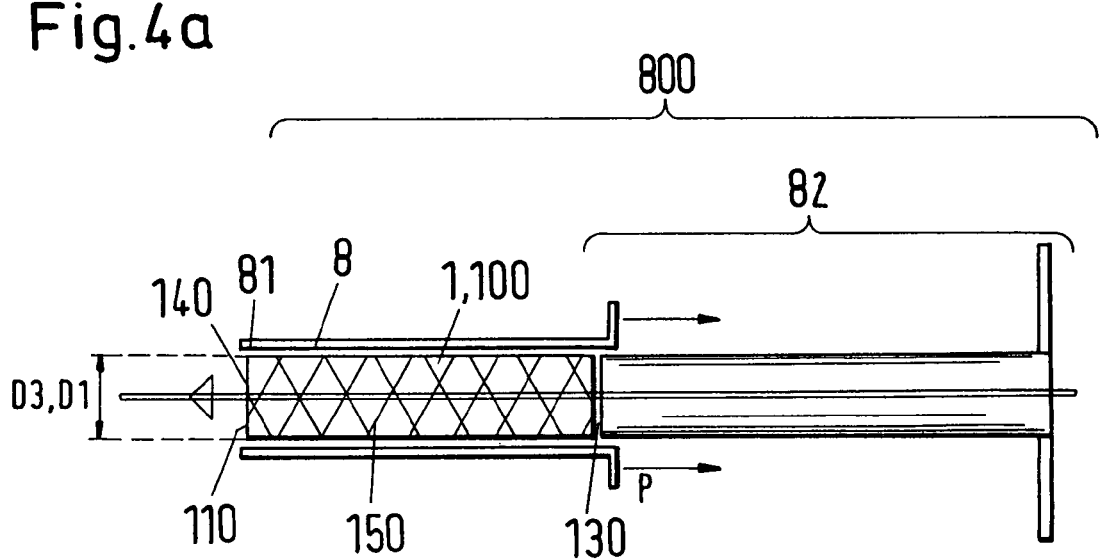
FIG. 4a shows a catheter-sheath-assembly.
Figure 4B:
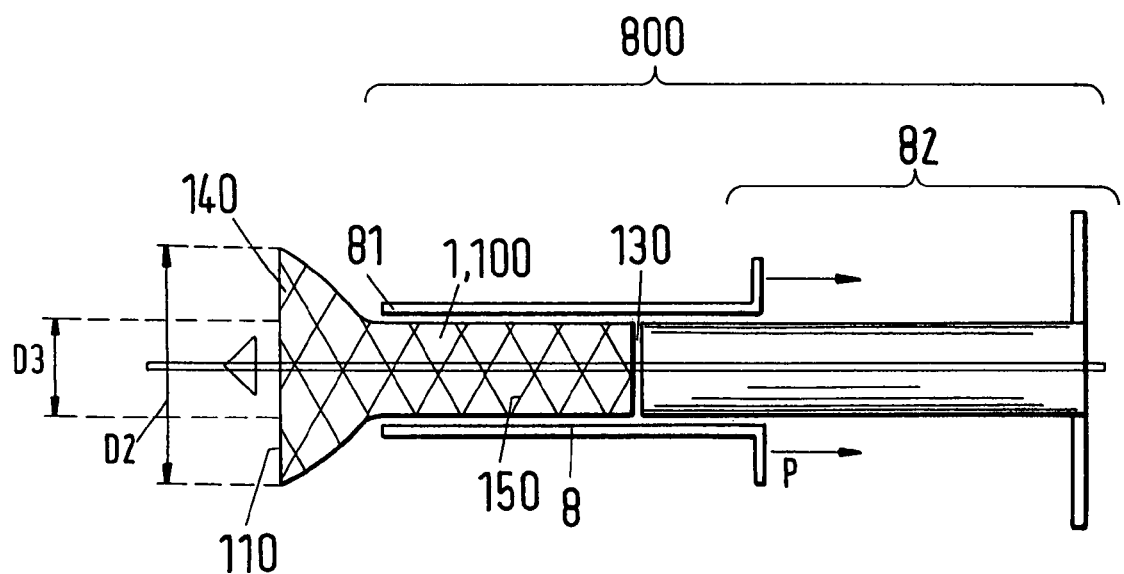
FIG. 4b shows a catheter-sheath-assembly according to FIG. 4a partly removed.
Figure 4C:
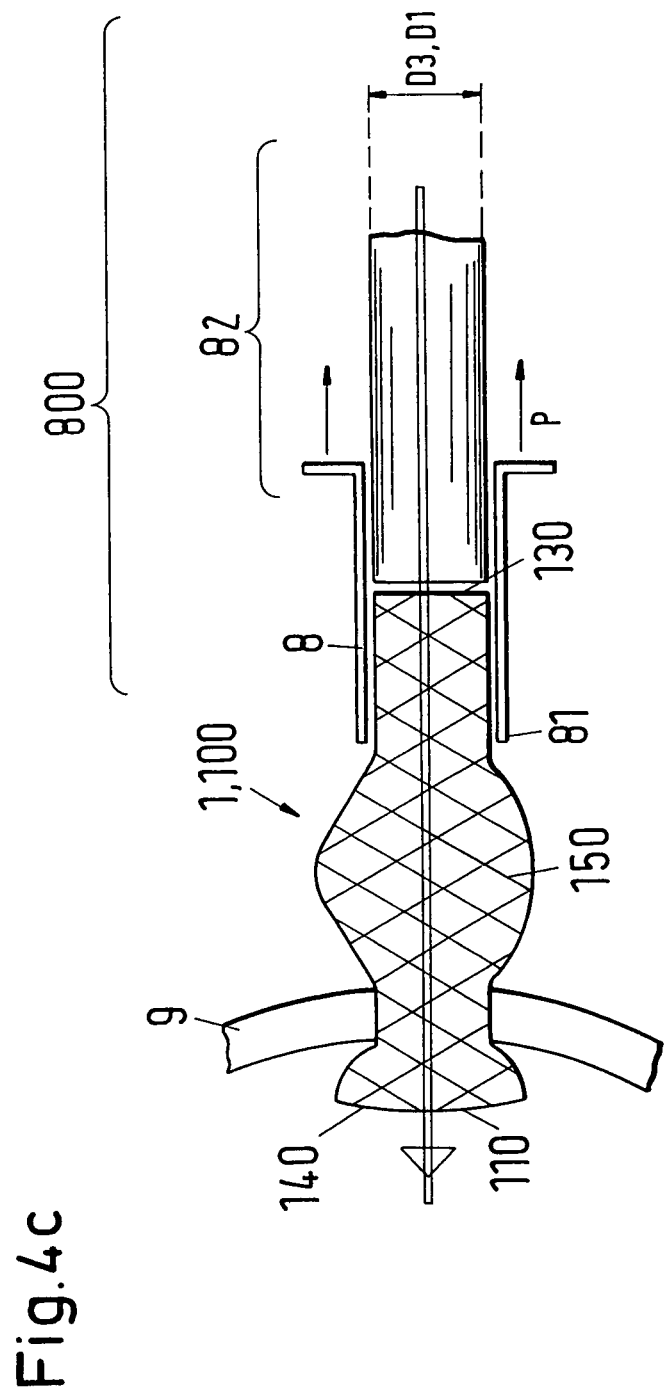
FIG. 4c shows a catheter-sheath-assembly according to FIG. 4a with the self-expanding cannula being attached to the wall of a heart.

FIGS. 4a-4c show a catheter-sheath-assembly 800 including a self-expanding cannula 1 assembled in a catheter-sheath 8 having a pusher-device 82 for removing the self-expanding cannula 1 after having it positioned within the corpus 2 of a patient.

The catheter-sheath-assembly 800 according to FIGS. 4a and 4b has not been introduced into a corpus 2 yet. The self-expanding cannula 1 is pre-assembled at a diameter D1, D3 into the catheter-sheath 8, wherein the diameter D3 of the self-expanding cannula 1 assembled in the catheter-sheath 8 may be equal or not equal to the diameter D1, wherein the diameter D3 may be in particular smaller or greater than the diameter D1 of the self-expanding cannula in the closed state. In a special embodiment, the catheter-sheath 8 may include a depth-marker, in particular a depth-marker-band for positioning a proximal-end 81 of the catheter-sheath 8 in the corpus 2. The embodiment shown in FIGS. 4a-4c does not include the depth-markers.

The catheter-sheath 8 according to FIGS. 4a-4c includes, as already mentioned, a pusher-device 82 for catheter-sheath 8 removal after positioning the self-expanding cannula 1 within the corpus 2.

Regarding FIG. 4a, the self-expanding cannula 1 is completely encompassed by the catheter-sheath 8 at a diameter D1, D3 and is ready for positioning within a corpus 2 of a patient.

FIG. 4b demonstrates how the pusher-device 82 works. Moving the pusher-device 82 along the arrow P, the catheter-sheath 8 is removed from the self-expanding cannula 1 and the self-expanding cannula 1 will expand to its opened diameter D2.

Regarding FIG. 4c, the self-expanding cannula 1 is introduced into the wall 9 of the heart of a patient and the catheter-sheath 8 is partly, but not completely, removed by the pusher-device 82 from the self-expanding cannula 1 after having positioned the self-expanding cannula 1 within the wall 9 of the heart.

That is, using a catheter-sheath 8 in accordance with the present invention allows to apply and position the self-expanding cannula 1 in a very easy and conservative way. That's why before positioning the self-expanding cannula 1 within the corpus 2, which self-expanding cannula 1 has in most cases a comparatively large opened diameter D2 in its opened state, the self-expanding cannula 1 assembled and compressed within the catheter-sheath 8, having a comparatively small diameter, is first positioned within the corpus 2 of the patient. Due to the small diameter of the catheter-sheath 8, which can be essentially nearly the same diameter as the closed diameter D1 of the self-expanding cannula 1, only a small tunnel through the skin 3 and the tissue of the corpus 2 is required ensuring a very conservative and easy way to tunnel the self-expanding cannula 1 to the tissue.

It is understood that the invention is not only related to the special embodiments discussed above but, of course, further embodiments are included, too. In particular, the invention relates to all advantageous combinations of the discussed embodiments.

Summarizing the discussion of the present invention, the self-expanding cannula according to the present invention is a wire braided tube covered with a flexible membrane so as to effect a leak-tight conduit and capable of passively expanding upon removal of a constricting outer catheter-sheath once advanced percutaneously through the skin into the body.

Although this device may be placed through traditional open chest methods, which are as such known from the state of the art, the primary benefit is its small profile, enabling it to be placed into the vasculature through normal Seldinger technique or modified Seldinger techniques and be advanced through the vasculature to a desired position within the heart. Optional fluoroscopic visualization may be utilized should end position require maneuvering within the atrium, ventricle or pulmonary vein. Proximal positioning may also be accomplished with the aid of a guide-wire or the guidance of a Swan-Ganz catheter previously positioned to a desired location.

Preferably, within the distal externalized portion of the cannula is a tissue dilating means provided to maintain the expandable cannula open as it transitions the vessel wall and surrounding muscle, fat and skin. The distal cannula end can be secured to an extracorporeal circuit. The device is "normally opened" but constrained by an outer sheath in the compressed compact state requiring minimal tissue puncture due to the small device profile. The device is passively dilated with the withdrawal of the sheath from the outside of the cannula.

The invention claimed is:

1. A method for positioning a self-expanding cannula within a human or an animal patient having a skin, the method comprising:
    positioning a proximal end of the self-expanding cannula in or adjacent a wall of the patient,
    the self-expanding cannula comprising a body encompassing a lumen, wherein the body of the self-expanding cannula is capable of passively expanding said lumen from a closed diameter to an opened diameter;
    positioning a distal end of the self-expanding cannula through the skin of the patient to externally communicate the lumen of the self-expanding cannula with an external environment outside of the patient; and
    securing the distal end of the self-expanding cannula to an extracorporeal fluid handling system located in the external environment outside of the patient;
    thereby defining an operative position of the self-expanding cannula wherein, in the operative position, the proximal end is positioned in or adjacent the wall, and the distal end protrudes through the skin to provide communication of the lumen of the self-expanding cannula with the fluid handling system located in the external environment outside of the patient.

2. The method of claim 1, wherein the organ or vessel wall of the patient comprises a wall of a heart or a blood vessel.

3. The method of claim 1, wherein the fluid handling system comprises a blood handling system.

4. The method of claim 1, wherein prior to the positioning steps, the self-expanding cannula is a part of an assembly comprising the self-expanding cannula, in the closed diameter, encased in a sheath.

5. The method of claim 4, wherein the sheath comprises a pusher device, and wherein the method further comprises removing the sheath from the self-expanding cannula by the pusher-device, such that the self-expanding cannula expands.

6. The method of claim 1, wherein the operative position further comprises an intermediate portion of the self-expanding cannula intermediate the proximal end and the distal end being disposed within a lumen of an additional vessel of the patient.

7. The method of claim 6, wherein the opened diameter of the self-expanding cannula is larger than a diameter of the lumen of the additional vessel, and wherein a rigidity of the self-expanding cannula is low enough that, in the operative position, the intermediate portion of the self-expanding cannula expands to an intermediate diameter intermediate the closed diameter and the opened diameter, wherein the intermediate diameter is substantially the same as the diameter of the lumen of the additional vessel.

8. The method of claim 1, wherein the organ or vessel wall of the patient is a wall of a heart, and wherein a rigidity of the self-expanding cannula is low enough that, in the operative position, the proximal end of the self-expanding cannula expands to an intermediate diameter intermediate the closed diameter and the opened diameter.

9. A self-expanding cannula, configured to provide a conduit through a skin between an inside of a corpus and an outside of the corpus, said self-expanding cannula comprising:
- a body encompassing a lumen, wherein the body comprises braided wire, and wherein the body is configured to passively expand from a closed diameter to an opened diameter, wherein a portion of the braided wire is covered by a flexible membrane, enabling the braided wire to articulate from the closed diameter to the opened diameter, the flexible membrane sealing an interstitial space resultant between the braid openings;
- a distal end of the body configured to be positioned outside of the corpus and configured for attachment to an extracorporeal fluid handling system; and
- a proximal end of the body configured to be positioned inside of the corpus, configured for attachment to an organ or a vessel of the corpus, wherein the proximal end of the self-expanding cannula comprises a bare section which does not contain the flexible membrane, in order to provide a flow of a fluid through said interstitial space resultant between the braid openings of said bare section.

10. The self-expanding cannula of claim 9, further comprising the fluid handling system, configured to be attached to the distal end of the self-expanding cannula.

11. The self-expanding cannula of claim 10, wherein the fluid handling system comprises a blood handling system.

12. The self-expanding cannula of claim 9, wherein a rigidity of the self-expanding cannula is low enough that, when the self-expanding cannula is placed within a blood vessel or through a wall of a heart in the closed position and allowed to expand, the self-expanding cannula expands to an intermediate diameter intermediate the closed diameter and the opened diameter.

13. The self-expanding cannula of claim 9, wherein the flexible membrane is positioned inside of the braided wire.

14. The self-expanding cannula of claim 9, wherein the flexible membrane is positioned outside of the braided wire.

15. The self-expanding cannula of claim 9, wherein the flexible membrane is positioned inside and outside of the braided wire.

16. The self-expanding cannula of claim 9, wherein individual wires of the braided wire of the bare section are individually coated.

17. The self-expanding cannula of claim 9, further comprising a sheath configured to house the self-expanding cannula in the closed diameter of the self-expanding cannula.

18. The self-expanding cannula of claim 9, further comprising a velour portion of the self-expanding cannula, contained within a velour-like tube.

19. The self-expanding cannula of claim 9, wherein the flexible membrane comprises at least one member of the group consisting of polyurethane, vinyl, a thermoplastic rubber, a natural rubber, and a thermoset material.

20. The self-expanding cannula of claim 9, wherein the wire is braided to a loose pitch ranging from 0.5" to 4".

21. The self-expanding cannula of claim 9, wherein the wire comprises at least one member of the group consisting of plastic, a composite material, and a metal.

* * * * *